US012797493B2

(12) United States Patent
Zhang et al.

(10) Patent No.: US 12,797,493 B2
(45) Date of Patent: Nov. 17, 2026

(54) GASTROINTESTINAL TRACT ULTRASONIC EXAMINATION AIDED DEVELOPER AND PREPARATION METHOD THEREFOR

(71) Applicant: Shandong Branden Medical Device Co., Ltd, Shandong (CN)

(72) Inventors: Haijun Zhang, Shandong (CN); Kunshan Yuan, Shandong (CN); Guixue Wang, Shandong (CN)

(73) Assignee: Shandong Branden Medical Device Co., Ltd., Shandong (CN)

( * ) Notice: Subject to any disclaimer, the term of this patent is extended or adjusted under 35 U.S.C. 154(b) by 463 days.

(21) Appl. No.: 18/537,834

(22) Filed: Dec. 13, 2023

(65) Prior Publication Data

US 2024/0123094 A1 Apr. 18, 2024

Related U.S. Application Data

(63) Continuation-in-part of application No. PCT/CN2023/087722, filed on Apr. 12, 2023.

(30) Foreign Application Priority Data

Oct. 12, 2022 (CN) ......................... 202211246992.7

(51) Int. Cl.
*A61K 49/22* (2006.01)

(52) U.S. Cl.
CPC .................................. *A61K 49/226* (2013.01)

(58) Field of Classification Search
CPC .... A61K 49/226; A61K 49/22; A61K 49/221; A61K 49/225
See application file for complete search history.

(56) References Cited

U.S. PATENT DOCUMENTS 5,107,842 A * 4/1992 Levene ................ A61K 49/226 600/458
2008/0281197 A1* 11/2008 Wiley ..................... C08L 71/02 600/437

FOREIGN PATENT DOCUMENTS

| | | |
|---|---|---|
| CN | 1721000 | 1/2006 |
| CN | 102068706 | 5/2011 |
| CN | 102441180 | 1/2013 |
| CN | 104043137 | 9/2014 |
| CN | 104524601 | 4/2015 |
| CN | 103611173 | 5/2015 |
| CN | 105079829 | 11/2015 |
| CN | 107055553 | 8/2017 |
| CN | 107115534 | 9/2017 |
| CN | 108046276 | 5/2018 |
| CN | 108939097 | 12/2018 |
| CN | 109745570 | 5/2019 |
| CN | 111214669 | 6/2020 |
| CN | 115300643 | 11/2022 |
| JP | 2009274923 | 11/2009 |

OTHER PUBLICATIONS

Catauro, M.; et al., Influence of the Polymer Amount on Bioactivity and Biocompatibility of SiO2/PEG hybrid materials synthesized by sol-gel technique, Mater. Sci. Eng. C, 2015; 48:548-555. (Year: 2015).*
Shuai Wang, "Functionalization mesoporous silica nanomaterials, drug loading and release studies in vitro", Thesis of Master Degree, Guizhou University, Jun. 2020, pp. 1-70.
Shi, Shaoming, "Research on Drug Delivery System Based on Mesoporous Silica", Thesis of Master Degree, Changzhou University, Jun. 2021, pp. 1-78.
Li, Shang-Ji, "Construction of Controlled Drug Delivery Systems Based on Aminated Mesoporous Silica/Biological Macromolecules", Thesis of Master Degree, Changzhou University, May 2021, pp. 1-81.
Cheng, Chun-Feng et al., "Preparation of Pickering emulsions with SiO2 nanoparticles activated with alginate derivative", China Surfactant Detergent & Cosmetics, vol. 44, No. 5, May 2014, pp. 241-246.
Liu, Wei-Kun et al., "Preparation of functionalized mesoporous silica nanoparticles loaded cisplatin and its killing effect on breast cancer cells", Journal of Taishan Medical College, vol. 40, No. 11, Nov. 7, 2019, pp. 801-805.
"International Search Report (Form PCT/ISA/210) of PCT/CN2023/087722," mailed on Jul. 11, 2023, pp. 1-5.

* cited by examiner

*Primary Examiner* — Sahana S Kaup
*Assistant Examiner* — Eric P. Mosher
(74) *Attorney, Agent, or Firm* — JCIPRNET

(57) ABSTRACT

Disclosed are a gastrointestinal tract ultrasonic examination aided developer and a preparation method therefor. The aided developer is mainly composed of a thickener, an osmotic pressure regulator, a solid contrast, a defoamer and a flavoring agent, wherein a density of the solid contrast is the same as that of aided developer liquid. The present disclosure adopts the solid contrast with a special particle size, making a distribution area present a more obvious homogeneous high echo after the aided developer reaches the stomach and intestine, and a good aided developing effect is achieved.

7 Claims, 2 Drawing Sheets

GASTROINTESTINAL TRACT ULTRASONIC EXAMINATION AIDED DEVELOPER AND PREPARATION METHOD THEREFOR

CROSS-REFERENCE TO RELATED APPLICATION

This application is a continuation-in-part of international application of PCT application serial no. PCT/CN2023/087722, filed on Apr. 12, 2023, which claims the priority benefit of China application no. 202211246992.7, filed on Oct. 12, 2022. The entirety of each of the above-mentioned patent applications is hereby incorporated by reference herein and made a part of this specification.

BACKGROUND

Technical Field

The present disclosure relates to a gastrointestinal tract ultrasonic examination aided developer and a preparation method therefor, belonging to the technical field of medical ultrasonic examination.

Description of Related Art

A gastrointestinal tract occupies ¾ of the volume of an abdominal cavity and constitutes the majority of a digestive tract. To clarify the location, nature and the like of the lesion, different examination methods are often used to assist in diagnosis. Methods for the gastrointestinal tract examination include upper gastrointestinal barium meal, gastroscopy, gastric computerized tomography (CT), magnetic resonance imaging (MRI), etc. The upper gastrointestinal barium meal is convenient, less in pain and is easy to accept by patients, however, barium meal examination has radioactivity, and the examination results are affected by barium agent coating, a filling effect, and experience of an examiner. Although barium sulfate is relatively safe, for a few patients, there may be adverse reactions and complications, such as allergy, barium poisoning, barium leakage, barium sulfate fecal stone incarceration, increased constipation, or even causing death, therefore its clinical application is limited, especially for the elderly, constipation patients and pregnant women, as well as patients with barium allergy and acute upper gastrointestinal bleeding and other patients. X-ray barium meal examination is not used as a routine aided diagnostic method. By the gastroscopy, the shape, color, lesion location, lesion size and lesion depth of gastric mucosa can be directly observed, the lesion can be seen under direct vision, and the lesion is taken for pathological examination to determine the nature of the lesion. However, the gastroscopy can only well show the structure in the cavity, while the hierarchy of the gastric wall and gastric peristalsis cannot be observed by the gastroscopy. Due to the fact that the gastroscopy is an interventional examination, most of people experience discomfort, such as elderly patients with severe heart and lung diseases who cannot tolerate gastroscope, patients in the acute stage of upper gastrointestinal perforation, patients with acute severe pharyngeal disease, patients in the acute stage of corrosive esophageal injury, and patients with mental disorders who cannot give cooperation, and therefore the application of the gastroscopy is subjectively and objectively limited. With a high spatial resolution and clear anatomical structure display, CT/MRI examination is a commonly used imaging detection method for gastric cancer staging. However, it is difficult to detect small lesions in the gastrointestinal cavity through the CT/MRI examination, so the CT/MRI examination has little diagnostic value for other gastrointestinal diseases and is not used as a routine examination method.

Since the discovery of piezoelectricity and anti-piezoelectricity in physics at the beginning of the 20th century, the history of ultrasonic technology has been quickly opened. Because of no invasion, no pain, low price, good tolerance and no radioactivity, it has become a common and important examination method in the substantive organs of the digestive system.

At present, the gastrointestinal ultrasonic examination in clinical application mainly includes three methods: transabdominal wall gastrointestinal ultrasonic examination, gastrointestinal filling ultrasonic examination, and ultrasonic endoscope examination. The transabdominal wall gastrointestinal ultrasonic examination is only used as the preliminary screening; the ultrasonic endoscope examination combines the advantages of endoscopy and ultrasound, makes up for their respective shortcomings and further improves the diagnostic level of the endoscopy and the ultrasound. However, due to its expensive price, complex operation, and certain trauma, it is only limited to some large hospitals and far from being popularized; the gastrointestinal filling ultrasonic examination is a method for improving the internal environment of gastrointestinal ultrasonic imaging so as to achieve a clearer display of a gastrointestinal wall structure and a lesion thereof by filling a contrast agent (also known as an aided developer) in the gastrointestinal cavity to eliminate the interference of gas and contents in the gastrointestinal cavity to ultrasound. This technology is a development trend for ultrasonic examination of gastrointestinal diseases, and can be popularized. The contrast agent mainly includes an echo-free water dosage form and an echo powder dosage form, and currently, the echo powder dosage form is mainly applied.

At present, the contrast agent in the Chinese market is mainly prepared by grinding, mixing and blending the existing local traditional Chinese medicine or food ingredients, for example, the aided developer prepared by using Chinese herbal formulas described in CN102441180B and CN103611173B and the like has a certain health and therapeutic effect. The aided developer described in CN1721000A is prepared by grinding, mixing and blending food ingredients, with a good ultrasonic image displaying effect. But it needs to be directly brewed with 90-100° C. boiling water before use and is quickly stirred to form a uniform paste solution, and then after cooling to a suitable temperature (usually controlled at 30-50° C.), the patient is advised to take the ultrasonic examination after drinking the aided developer or take the ultrasonic examination while drinking the aided developer.

In addition to the traditional Chinese medicine or food aided developers, the aided developer that is more convenient to use and better in effect has been developed. For example, in patent CN107115534A, an aided developer with a good compatibility and a filling effect is obtained through the combination of an osmotic pressure contrast agent, a swelling substance, a stabilizer and a defoamer. In patent CN109745570A, besides use of an osmotic pressure contrast agent, a solid contrast is added to increase the development effect, and bioactive substances such as bioactive glass, fructooligosaccharide and hyaluronic acid are introduced to play a certain role in health care.

However, there are certain limitations for various types of aided developers, for example the traditional Chinese medicine aided developer has a good health effect, but its display interface under the ultrasound is a low-echo interface with a limited aided developing effect; the food ingredient aided developer is complicated to operate and long in waiting time; the aided developer added with the solid contrast firstly needs an appropriate solid contrast particle size, the developing effect is not good if the solid contrast particle is too small or too large, the brightness of the developing interface is too low if the solid contrast particle is too small, and the particle feeling of the developing interface is too strong if the solid contrast particle is too large. In addition, a density of the solid contrast should be matched with an aided developer liquid system, the mismatched density will affect the uniformity of the product. The solid contrast in the liquid aided developer is prone to sinking if the density is too high, while the solid contrast in the liquid aided developer is prone to floating if the density is too low. Finally, the aided developer needs to be added with the swelling substance to increase the window period, however when the aided developer system remains a high viscosity, the gas in the stomach and intestine is difficult to discharge, easily causing artifacts and affecting the developing effect, moreover when the solid contrast sinks or floats due to a too high density or a too low density, it is difficult to shake well. When the aided developer system remains a low viscosity, it easily leads to a too short window period, and the stomach and intestine quickly empty the aided developer, thereby causing difficulties to the gastrointestinal ultrasonic diagnosis work of clinical doctors.

SUMMARY

For the shortcomings of the above-mentioned existing technology, the objective of the present disclosure is to provide a gastrointestinal tract ultrasonic examination aided developer which has a stronger aided developing effect, is a stable and uniform product, and not only is easy to discharge excessive gas in the gastrointestinal tract, but also increases the window period of the gastrointestinal tract during use.

In order to achieve the above objective, the present disclosure adopts the following technical solution:

A gastrointestinal tract ultrasonic examination aided developer, where it is prepared by the following components in parts by weight: 2-4 parts of thickener, 2-4 parts of osmotic pressure regulator, 1.5-2.5 parts of solid contrast, 0.02-0.04 parts of defoamer, 0.03-0.05 parts of flavoring agent, 0.03-0.05 parts of preservative and 89.36-94.42 parts of pure water; and a density of the solid contrast is the same as that of the aided developer liquid, which is 1.028 g/ml-1.089 g/ml.

Further, the thickener is one or more of Poloxamer 407, Poloxamer 338, Poloxamer 237 and Poloxamer 188.

Further, the osmotic pressure regulator is at least one of xylitol and mannitol.

Further, the solid contrast is a silica particle modified by a biocompatible polymer; and the biocompatible polymer is one or more of polyethylene glycol, branched polyethylene glycol, chitosan, alginic acid, hyaluronic acid and polysiloxane.

Further, a method for modifying the silica particle with the biocompatible polymer is one or more of a sol-gel method, a one-step post-synthesis method, a two-step post-synthesis method, and a site selection post-synthesis method.

Further, the silica particle is prepared by mixing silica particles with different particle sizes mixed in a specific ratio, and a specific formula is as follows: the silica particles with particle sizes of 75-85 meshes (excluding 85 meshes), 85-95 meshes (excluding 95 meshes), 95-105 meshes (excluding 105 meshes) and 105-120 meshes are evenly mixed in a mass ratio of (60-65):(15-20):(5-10):(5-20).

Further, the defoamer is at least one of an organosilicon defoamer and a polyether defoamer, the organosilicon defoamer may be dimethylsiloxane and the like, and the polyether defoamer may be polyoxypropylene oxyethylene glycol ether and the like.

Further, the flavoring agent is one or more of strawberry essence, lemon essence and apple essence.

Further, the preservative is deoxidized sodium acetate.

Further, a gel temperature of the aided developer is 20-30° C., a viscosity of the aided developer is relatively low when the temperature is lower than the gel temperature, and the viscosity of the aided developer increases when the temperature is higher than the gel temperature.

Further, the viscosity of the aided developer at 20±0.2° C. is less than or equal to 100 mPa·s, and the viscosity of the aided developer at 37±0.2° C. is more than or equal to 500 mPa·s.

In the present disclosure, a specific proportion of the silica particles with different particle sizes are used to optimize the developing effect, to ensure that the aided developer shows a good aided developing effect on an ultrasonic image interface; the silica particles are modified by the biocompatible polymers, making the density thereof be the same as that of the aided developer liquid and no settling generate during the storage, such that the stability of the product is ensured; the temperature-sensitive thickener is selected, so a low viscosity is presented at a normal temperature and a high viscosity is presented at 37° C., the entire temperature is relatively low at the beginning of the aided developer reaching the stomach and intestine, a low viscosity state benefits for the discharge of the gas in the stomach and intestine and can reduce the artifacts caused by the gas residue; after the aided developer reaches the stomach and intestine for a period of time, the entire temperature rises to a body temperature, and the viscosity increases, so that the examination window period of the stomach and intestine is prolonged, thereby ensuring the sufficiency of the examination time.

Further, a preparation method for the gastrointestinal tract ultrasonic examination aided developer, comprising the following steps of: taking pure water, controlling a temperature of the pure water to 2-4° C., slowly adding a thickener, a defoamer, a flavoring agent and a preservative in turn at 800-1200 rpm, then adjusting a rotation speed to 50-100 rpm, slowly adding a solid contrast, then adjusting the rotation speed to 800-1200 rpm, adding an osmotic pressure regulator, stirring for 20-40 min, and finally subpackaging to a 500 ml of brown polyester bottle, so as to obtain the gastrointestinal tract ultrasonic examination aided developer.

The present disclosure has the beneficial effects:

1. The aided developer of the present disclosure has a good aided developing effect. Through a large number of in vitro and in vivo experiments, it has verified that the developing effect is optimized by using a specific proportion of silica particles with different particle sizes, thereby ensuring that the aided developer shows a good aided developing effect on an ultrasonic image interface.
2. The aided developer of the present disclosure does not generate the floating or sinking of the solid contrast, thereby ensuring the uniform stability of the product. The silica particles are modified by using the biocompatible polymer, making the density thereof be the same as that of the aided developer liquid, and the floating or sinking does not occur during a storage process, so the stability of the product is ensured.

3. The aided developer of the present disclosure can discharge the excessive gas in the stomach and intestine while ensuring the enough window period, thereby reducing the influence of gas artifacts on the aided developing effect of the gastrointestinal ultrasonic diagnosis. The temperature-sensitive thickener is used, the low viscosity is presented at a normal temperature and the high viscosity is presented at 37° C.; the entire temperature is relatively low at the beginning of the aided developer reaching the stomach and intestine, the low viscosity state benefits for the discharge of the gas in the stomach and intestine, and can reduce the artifact problem caused by gas residue. After the aided developer reaches the stomach and intestine for a period of time, the entire temperature rises to the body temperature, the viscosity increases, so that the examination window period of the stomach and intestine is prolonged, thereby ensuring the sufficiency of the examination time.

DESCRIPTION OF THE EMBODIMENTS

Figure 1:
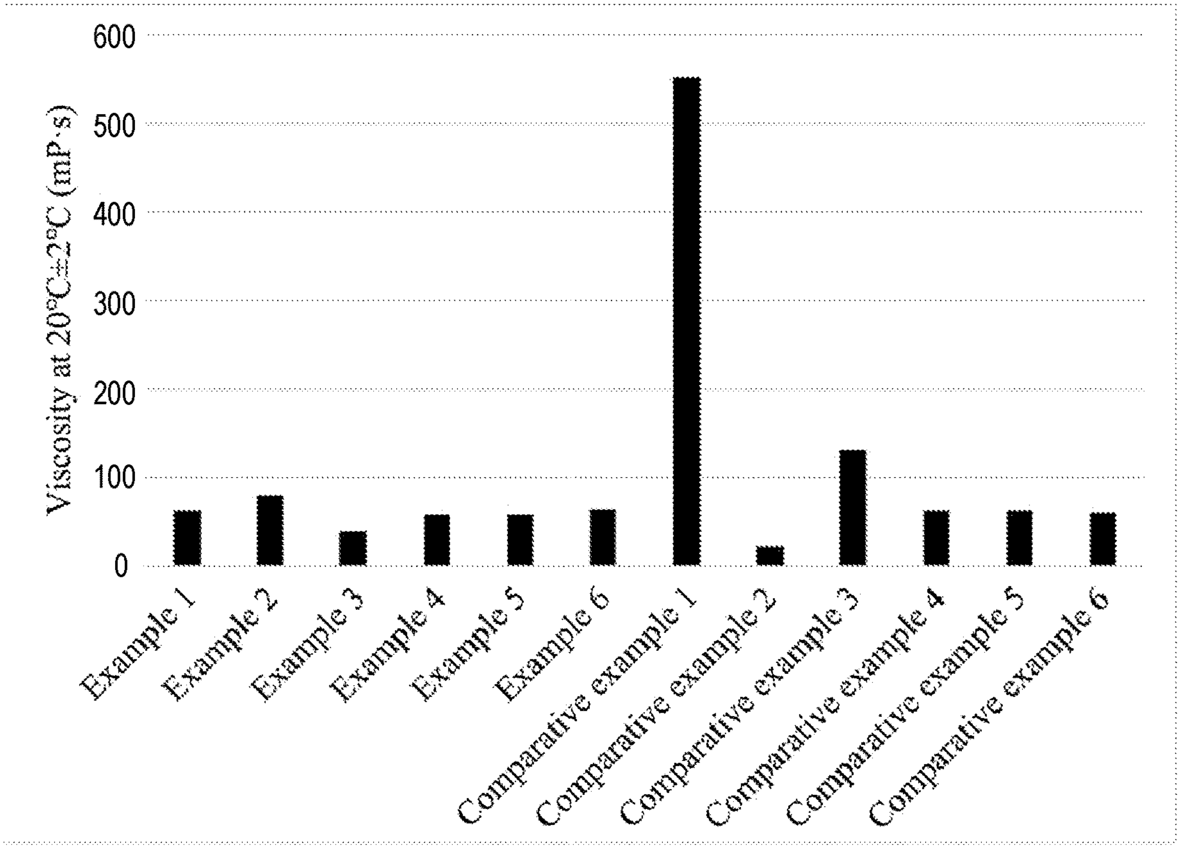
FIG. 1 is a viscosity graph of gastrointestinal tract ultrasonic examination aided developers prepared in various examples and comparative examples at 20° C.±0.2° C. according to the present disclosure.

Next, the present disclosure will be further illustrated in combination with examples. It should be noted that the following description is only for explaining the present disclosure but not limiting the contents of the present disclosure.

Poloxamer 407, Poloxamer 338, Poloxamer 237 and Poloxamer 188 used in examples and comparative examples are all commercially available.

Example 1

91.84 g of pure water was taken, a temperature of the pure water was controlled at 2-4° C., 2.7 g of Poloxamer 338, 0.35 g of Poloxamer 188, 0.03 g of dimethylsiloxane, 0.04 g of lemon essence and 0.04 g of deoxygenated sodium acetate were slowly added in turn at 800-1200 rpm, then a rotation speed was adjusted to 50-100 rpm, and 2 g of polyethylene glycol modified silica particles with a density of 1.06 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 62.5:17.5:7.5:12.5, subsequently the rotation speed was adjusted to 800-1200 rpm, 3 g of xylitol was added to be stirred for 20-40 min, and finally the obtained mixture was subpackaged into a brown polyester bottle, so as to obtain a gastrointestinal tract ultrasonic examination aided developer.

Example 2

89.41 g of pure water was taken, a temperature of the pure water was controlled at 2-4° C., 3.7 g of Poloxamer 407, 0.25 g of Poloxamer 188, 0.04 g of polyoxypropylene oxyethylene glycol ether, 0.05 g of strawberry essence and 0.05 g of deoxygenated sodium acetate were slowly added in turn at 800-1200 rpm, then a rotation speed was adjusted to 50-100 rpm, and 2.5 g of chitosan modified silica particles with a density of 1.089 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 60:15:5:20, subsequently the rotation speed was adjusted to 800-1200 rpm, 4 g of mannitol was added to be stirred for 20-40 min, and finally the obtained mixture was subpackaged into a brown polyester bottle, so as to obtain a gastrointestinal tract ultrasonic examination aided developer.

Example 3

94.42 g of pure water was taken, a temperature of the pure water was controlled at 2-4° C., 2 g of Poloxamer 407, 0.02 g of dimethylsiloxane, 0.03 g of apple essence and 0.03 g of deoxygenated sodium acetate were slowly added in turn at 800-1200 rpm, then a rotation speed was adjusted to 50-100 rpm, and 1.5 g of alginic acid modified silica particles with a density of 1.028 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 65:20:10:5, subsequently the rotation speed was adjusted to 800-1200 rpm, 2 g of xylitol was added to be stirred for 20-40 min, and finally the obtained mixture was subpackaged into a brown polyester bottle, so as to obtain a gastrointestinal tract ultrasonic examination aided developer.

Example 4

93.39 g of pure water was taken, a temperature of the pure water was controlled at 2-4° C., 2.5 g of Poloxamer 338, 0.5 g of Poloxamer 237, 0.03 g of dimethylsiloxane, 0.04 g of lemon essence and 0.04 g of deoxygenated sodium acetate were slowly added in turn at 800-1200 rpm, then a rotation speed was adjusted to 50-100 rpm, and 1.5 g of hyaluronic acid modified silica particles with a density of 1.044 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 62.5:17.5:7.5:12.5, subsequently the rotation speed was adjusted to 800-1200 rpm, 2 g of xylitol was added to be stirred for 20-40 min, and finally the obtained mixture was subpackaged into a brown polyester bottle, so as to obtain a gastrointestinal tract ultrasonic examination aided developer.

Example 5

90.39 g of pure water was taken, a temperature of the pure water was controlled at 2-4° C., 2.9 g of Poloxamer 407, 0.1 g of Poloxamer 237, 0.03 g of dimethylsiloxane, 0.04 g of lemon essence and 0.04 g of deoxygenated sodium acetate were slowly added in turn at 800-1200 rpm, then a rotation speed was adjusted to 50-100 rpm, and 2.5 g of polysiloxane modified silica particles with a density of 1.078 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 62.5:17.5:7.5:12.5, subsequently the rotation speed was adjusted to 800-1200 rpm, 4 g of xylitol was added to be stirred for 20-40 min, and finally the obtained mixture was subpackaged into a brown polyester bottle, so as to obtain a gastrointestinal tract ultrasonic examination aided developer.

Example 6

91.85 g of pure water was taken, a temperature of the pure water was controlled at 2-4° C., 2.7 g of Poloxamer 407, 0.35 g of Poloxamer 188, 0.02 g of dimethylsiloxane, 0.03 g of lemon essence and 0.05 g of deoxygenated sodium acetate were slowly added in turn at 800-1200 rpm, then a rotation speed was adjusted to 50-100 rpm, and 2 g of branched polyethylene glycol modified silica particles with a density of 1.061 g/ml was slowly added, where the silica particles were prepared by evenly mixing silica particles with 75-85 meshes (excluding 85 meshes), silica particles with 85-95 meshes (excluding 95 meshes), silica particles with 95-105 meshes (excluding 105 meshes) and silica particles with 105-120 meshes (excluding 120 meshes) in a mass ratio of 62.5:17.5:7.5:12.5, subsequently the rotation speed was adjusted to 800-1200 rpm, 3 g of xylitol was added to be stirred for 20-40 min, and finally the obtained mixture was subpackaged into a brown polyester bottle, so as to obtain a gastrointestinal tract ultrasonic examination aided developer.

Comparative Example 1

Each step is the same as that in example 1 except that the thickeners are 1.35 g of sodium carboxymethyl cellulose, 1.35 g of hydroxypropylcellulose and 0.35 g of sodium hyaluronate.

Comparative Example 2

Each step is the same as that in example 1 except that the thickeners are 0.7 g of Poloxamer 338 and 0.15 g of Poloxamer 188.

Comparative Example 3

Each step is the same as that in example 1 except that the thickeners are 4.7 g of Poloxamer 338 and 0.65 g of Poloxamer 188.

Comparative Example 4

Each step is the same as that in example 1 except that the solid contrast silica particle is not subjected to the biocompatible polymer modification.

Comparative Example 5

Each step is the same as that in example 1 except that the particle sizes of the solid contrast silica particles are all 75-85 meshes.

Comparative Example 6

Each step is the same as that in example 1 except that the particle sizes of the solid contrast silica particles are all 105-120 meshes.

The silica particle modified by the biocompatible polymer can be prepared by referring to the methods described in "Functionalization Mesoporous Silica Nanomaterials, Drug Loading and Release Studies In Vitro" (Wang Shuai. Functionalization Mesoporous Silica Nanomaterials, Drug Loading and Release Studies In Vitro [D]. Guizhou University, 2020), "Thiol Carboxyl Double-modified Mesoporous Silica Nanoparticles and Preparation Method Therefor" (CN107055553A) "Preparation and Application of Carboxyl-Terminated Polyethylene Glycol Modified Mesoporous Silica Nanoparticles" (CN108046276A), "Research on Drug Delivery System Based on Mesoporous Silica" (Shi Shaoming. Research on Drug Delivery System Based on Mesoporous Silica [D]. Changzhou University, 2021), "Construction of Controlled Drug Delivery Systems Based on Aminated Mesoporous Silica/Biological Macromolecules" (Li Shangji. Construction of Controlled Drug Delivery Systems Based on Aminated Mesoporous Silica/Biological Macromolecules [D]. Changzhou University, 2021), "Preparation of Pickering emulsions with $SiO_2$ nanoparticles activated with alginate derivative" (Cheng Chun-feng, Li Jia-cheng, Yan Hui-qiong, Liu Ruo-lin, Wang Chun-xiu, Lin Qiang. Preparation of Pickering emulsions with $SiO_2$ nanoparticles activated with alginate derivative China Surfactant Detergent & Cosmetics, 2014, 44 (05): 241-246.), "Preparation of Functionalized Mesoporous Silica Nanoparticles Loaded Cisplatin and Its Killing Effect on Breast Cancer Cells" (Liu Wei-kun, Zhang Meng, Li Bing-long, Guan Xi-dong, Sun Ming-shuang, He Yu-jing, Wang Chunxiao, Zhao Bao-chang, Zhang Ji-mei. Preparation of Functionalized Mesoporous Silica Nanoparticles Loaded Cisplatin and Its Killing Effect on Breast Cancer Cells Journal of Taishan Medical College, 2019, 40 (11): 801-805.), etc.

According to the "YY/T 0681.1-2018 Test Methods for Sterile Medical Device Packaging-Part 1: Guidelines for Accelerated Aging Testing", with a 2-year validity period as the goal, the gastrointestinal ultrasonic examination aided developers prepared in example 1-6 and comparative example 1-6 were subjected to accelerated aging at 60° C. for 65 days, and the uniformity of the samples after aging was recorded. The results are seen in Table 1 below.

TABLE 1

Uniformity of samples after accelerated aging

| Grouping | Uniformity of samples after accelerated aging | Note |
|---|---|---|
| Example 1 | Uniform | / |
| Example 2 | Uniform | / |
| Example 3 | Uniform | / |
| Example 4 | Uniform | / |

TABLE 1-continued

| Uniformity of samples after accelerated aging | | |
|---|---|---|
| Grouping | Uniformity of samples after accelerated aging | Note |
| Example 5 | Uniform | / |
| Example 6 | Uniform | / |
| Comparative example 1 | Uniform | / |
| Comparative example 2 | non-uniform | Sinking of solid particles |
| Comparative example 3 | non-uniform | Floating of solid particles |
| Comparative example 4 | non-uniform | Sinking of solid particles |
| Comparative example 5 | Uniform | / |
| Comparative example 6 | Uniform | / |

It can be seen from Table 1 that the samples after accelerated aging in examples 1-6, comparative example 1, comparative example 5 and comparative example 6 are uniform, without the floating or sinking of solid particles. The densities of polyethylene glycol modified silica particles in comparative example 2 and silica particles not modified by the biocompatible polymer in comparative example 4 are both higher than the liquid density of the corresponding sample, and therefore the sinking of solid particles occurs, showing the non-uniformity phenomenon of the sample. The density of polyethylene glycol modified silica particles in comparative example 3 is lower than the liquid density of the corresponding sample, and therefore the floating of the solid particles occurs, showing non-uniformity phenomenon of the sample.

Figure 2:
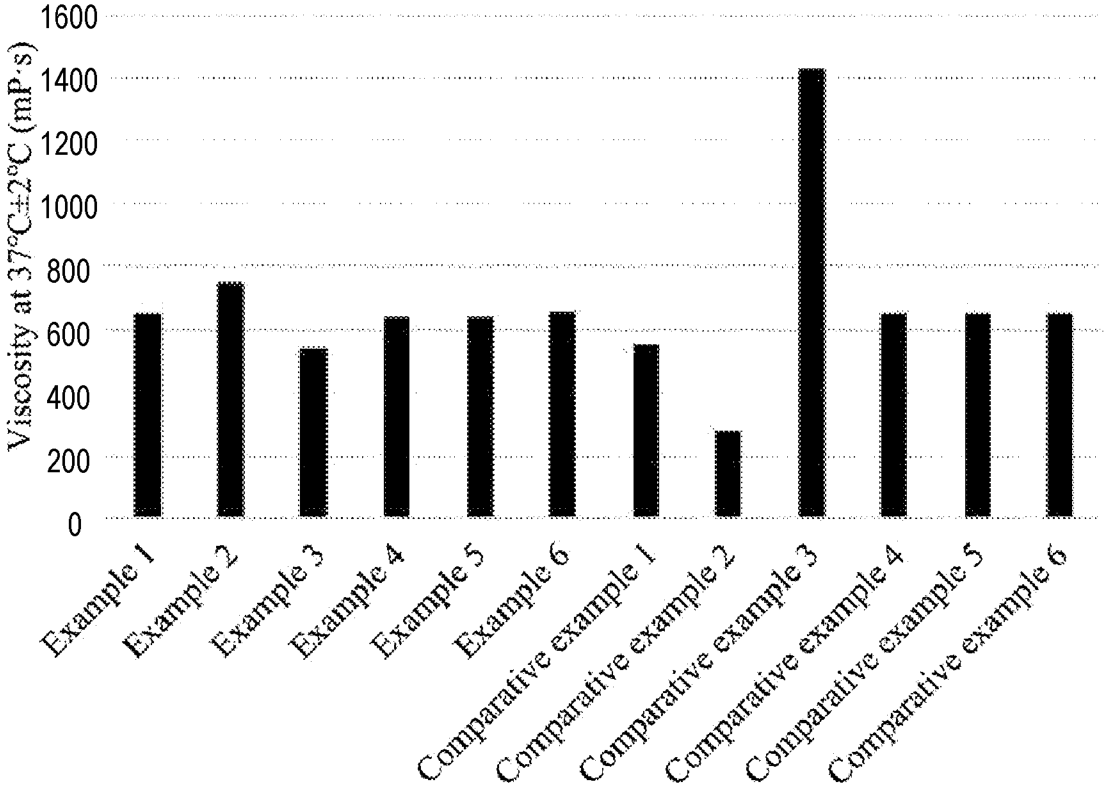
FIG. 2 is a viscosity graph of gastrointestinal tract ultrasonic examination aided developers prepared in various examples and comparative examples at 37° C.±0.2° C. according to the present disclosure.

The viscosities of the gastrointestinal tract ultrasonic examination aided developers prepared in examples 1-6 and comparative examples 1-6 at 20±0.2° C. and 37° C.±0.2° C. were measured, as shown in FIG. 1 and FIG. 2.

It can be seen from FIG. 1 and FIG. 2 that the viscosities of the gastrointestinal tract ultrasonic examination aided developers prepared in examples 1-6 and comparative examples 4-6 at 20±0.2° C. were all less than 100 mPa·s, and the viscosities at 37° C.±0.2° C. were all more than 500 mPa·s; in comparative example 1, since the thickener is a non-temperature-sensitive material, the viscosities thereof at 20±0.2° C. and 37±0.2° C. are not greatly different and all between 500 Pa·s and 600 mPa·s. In comparative example 2, since the addition amount of the thickener is relatively low, the viscosity thereof at 37±0.2° C. is less than 300 mPa·s. In comparative example 3, since the addition amount of the thickener is relatively high, the viscosity thereof at 20±0.2° C. is more than 130 mPa s.

The developing effects of the gastrointestinal tract ultrasonic examination aided developers prepared in examples 1-6 and comparative examples 1-6 were detected, and the specific method was as follows:

4 bottles of 500 ml samples were prepared for each group and stored in an environment of 20±0.2° C. Experimental animals were 4 beagle dogs, female 2/male 2, 9-11 months old, weighing around 10 kg, 500 ml of sample with a temperature of 20±0.2° C. was administered by gavage 15 minutes before imaging examination. The gastric and duodenal fullness was observed by ultrasonic examination.

Scores are given from 0 to 5 in terms of the hierarchy and structure of the gastric and duodenal wall, the gastric and duodenal morphology, the display of peristalsis and emptying function, window time satisfaction, and the effect of eliminating gas artifacts. The scoring criteria are shown in Table 2, and the higher the score, the better the ability.

TABLE 2

| Effect scoring standard | | |
|---|---|---|
| Items | Score | Judgment criteria |
| Hierarchy and structure | 0 score | The hierarchy and structure of the gastrointestinal wall cannot be completely observed. |
| | 1 score | The hierarchy and structure of the gastrointestinal wall can be observed, but is difficultly distinguished. |
| | 2 scores | The hierarchy and structure of the gastrointestinal wall may be difficultly distinguished to a certain degree. |
| | 3 scores | The hierarchy and structure of the gastrointestinal wall may be distinguished to a certain degree. |
| | 4 scores | The hierarchy and structure of the gastrointestinal wall may be distinguished more clearly. |
| | 5 scores | The hierarchy and structure of the gastrointestinal wall may be completely and clearly distinguished. |
| Morphology | 0 score | The gastrointestinal morphology cannot be completely observed. |
| | 1 score | The morphology of the stomach and intestine can be observed, but is difficultly distinguished. |
| | 2 scores | The morphology of the stomach and intestine may be difficultly distinguished to a certain degree. |
| | 3 scores | The morphology of the stomach and intestine may be distinguished to a certain degree. |
| | 4 scores | The morphology of the stomach and intestine may be distinguished more clearly. |
| | 5 scores | The morphology of the stomach and intestine may be completely and clearly distinguished. |
| Peristaltic and evacuation function display | 0 score | The peristaltic and evacuation function of the stomach and intestine cannot be completely observed. |
| | 1 score | The peristaltic and evacuation function of the stomach and intestine can be observed, but is difficultly judged. |
| | 2 scores | The peristaltic and evacuation function of the stomach and intestine may be more difficultly judged to a certain degree. |

TABLE 2-continued

| Effect scoring standard | | |
|---|---|---|
| Items | Score | Judgment criteria |
| | 3 scores | The peristaltic and evacuation function of the stomach and intestine may be distinguished to a certain degree. |
| | 4 scores | The peristaltic and evacuation function of the stomach and intestine may be distinguished more clearly. |
| | 5 scores | The peristaltic and evacuation function of the stomach and intestine is completely and clearly distinguished to a certain degree. |
| Satisfaction degree of effective examination window time | 0 score | The stomach window time cannot completely meet the observation requirement. |
| | 1 score | The stomach window time still has great shortage for the observation requirement. |
| | 2 scores | The stomach window time can meet the observation requirement as soon as possible to a certain extent. |
| | 3 scores | The stomach window time just meets the observation requirement at the normal speed. |
| | 4 scores | The relatively sufficient stomach window time is available to meet the observation requirement at normal the speed. |
| | 5 scores | The sufficient stomach window time is available to meet the observation requirement at the normal speed. |
| Elimination of gas artifact effect | 0 score | The gas artifact cannot be completely eliminated. |
| | 1 score | The gas artifact can be slightly eliminated, but the gas artifact still affects the ultrasonic observation on the stomach and intestinet. |
| | 2 scores | The gas artifact can be moderately eliminated, but the ultrasonic observation on the stomach and intestine by the gas artifact is limited. |
| | 3 scores | The gas artifact can be moderately eliminated, but the gas artifact has on influence on the ultrasonic observation. |
| | 4 scores | The gas artifact can be observably eliminated. |
| | 5 scores | The gas artifact can be completely eliminated. |

The developing effects in examples 1-6 and comparative examples 1-6 are seen in Table 3 below.

TABLE 3

| Developing effect | | | | | | |
|---|---|---|---|---|---|---|
| Group | Hierarchy and structure | Morphology | Peristaltic and evacuation function display | Satisfaction degree of effective examination window time | Elimination of gas artifact effect | Average scores |
| Example 1 | 5 | 5 | 5 | 5 | 5 | 5 |
| Example 2 | 4.75 | 5 | 5 | 5 | 5 | 4.95 |
| Example 3 | 5 | 5 | 5 | 4.75 | 5 | 4.95 |
| Example 4 | 5 | 5 | 5 | 4.75 | 5 | 4.95 |
| Example 5 | 4.75 | 5 | 5 | 5 | 5 | 4.95 |
| Example 6 | 5 | 5 | 5 | 5 | 5 | 5 |
| Comparative example 1 | 1 | 2.75 | 3 | 5 | 0 | 2.35 |
| Comparative example 2 | 2 | 3 | 2.75 | 1.25 | 3 | 2.4 |
| Comparative example 3 | 1 | 3 | 3 | 3 | 0 | 2 |
| Comparative example 4 | 2.75 | 3 | 2.75 | 3 | 3.25 | 2.95 |
| Comparative example 5 | 2.75 | 3.75 | 4 | 5 | 5 | 4.1 |
| Comparative example 6 | 3 | 4 | 3.75 | 5 | 5 | 4.15 |

It can be seen from Table 3 that the average score of examples 1-6 exceeded 4.9 scores. From various scores, it can be seen that the developing effects of the samples in examples 1-6 are as follows: the hierarchy and structure of the gastrointestinal wall, the morphologies of various parts of the stomach and intestine, gastrointestinal peristalsis and evacuation function can be almost completely clearly distinguished; the gas artifact can be completely eliminated; there is sufficient gastric window time, which may meet the needs of observation at a normal speed. The average scores of comparative example 1, comparative example 2, comparative example 3 and comparative example 4 are 2.35, 2.4, 2 and 2.95 respectively, which are far less than scores of examples 1-6. It can be seen from scores of various items that due to the use of ordinary thickeners in comparative example 1, in order to ensure the window period of the sample, its viscosity is equivalent to the final viscosity of the aided developer described in examples 1-6 when it reaches the stomach. However, the viscosity is not changed from 20±0.2° C. to 37±0.2° C. Therefore, it is difficult to discharge the gas from the stomach and intestine at this viscosity, and the ultrasonic image shows a large amount of gas artifact interference. Therefore, except for the high score during the window period, all other scores are lower. Although there is an increase in viscosity from 20±0.2° C. to 37° C.±0.2° C. in comparison examples 2 and 3, the viscosity at 20±0.2° C. is also too low or high due to the too low or high amount of thickener added. In addition, the density of solid particles is different from the density of the sample liquid. Even if the product is shaken well, there is still an issue of uneven ultrasonic imaging when it reaches the stomach, so the overall score is relatively low. The solid contrast in comparative example 4 is not modified by the biocompatible polymer, so it is prone to settling even in the stomach, resulting in uneven display of high echo interfaces at the gastrointestinal ultrasonic interface. Therefore, its various scores are relatively low. The average scores of comparative example 5 and comparative example 6 were 4.1 and 4.15, respectively, which were relatively high. However, by observing various scores, it can be known that the solid contrast particles in comparative example 5 and comparative example 6 are not mixed with different particle sizes of silica in a certain proportion, so their particle scattering and reflection are single. The hierarchy and structures of the gastrointestinal wall, the morphologies of various parts of the stomach and intestine, gastrointestinal peristalsis and evacuation function scores in the imaging effect are lower than those in examples.

The above examples are only some examples of the present disclosure, but not all the examples. The detailed description of the embodiments of the present disclosure are intended to only express the selected embodiments of the present disclosure rather than limiting the scope of protection of the present disclosure. Based on the embodiments of the present disclosure, other embodiments obtained by persons of ordinary skill in the art without contributing creative efforts are all included within the scope of protection of the present disclosure.

What is claimed is:

1. A gastrointestinal tract ultrasonic examination aided developer, consisting of the following components in parts by weight:

2-4 parts of a thickener, which is one or more of Poloxamer 407, Poloxamer 338, Poloxamer 237 and Poloxamer 188;

2-4 parts of an osmotic pressure regulator;

1.5-2.5 parts of a solid contrast;

0.02-0.04 parts of a defoamer;

0.03-0.05 parts of a flavoring agent;

0.03-0.05 parts of a preservative, which is deoxidized sodium acetate; and 89.36-94.42 parts of pure water, wherein a density of the solid contrast is the same as that of the gastrointestinal tract ultrasonic examination aided developer, wherein the solid contrast are silica particles modified by a biocompatible polymer, the biocompatible polymer is one or more of polyethylene glycol, branched polyethylene glycol, chitosan, alginic acid, hyaluronic acid and polysiloxane, and the silica particles have different particle sizes as follows:

the silica particles with particle sizes of 75-85 meshes, 85-95 meshes, 95-105 meshes and 105-120 meshes are mixed in a mass ratio of (60-65):(15-20):(5-10):(5-20).

2. The gastrointestinal tract ultrasonic examination aided developer according to claim 1, wherein the osmotic pressure regulator is at least one of xylitol and mannitol.

3. The gastrointestinal tract ultrasonic examination aided developer according to claim 1, wherein a method for modifying the silica particles with the biocompatible polymer is one or more of a sol-gel method, a one-step post-synthesis method, a two-step post-synthesis method, and a site selection post-synthesis method.

4. The gastrointestinal tract ultrasonic examination aided developer according to claim 1, wherein the defoamer is at least one of an organosilicon defoamer and a polyether defoamer; and the flavoring agent is one or more of strawberry essence, lemon essence and apple essence.

5. The gastrointestinal tract ultrasonic examination aided developer according to claim 4, wherein the organosilicon defoamer is dimethylsiloxane, and the polyether defoamer is polyoxypropylene oxyethylene glycol ether.

6. The gastrointestinal tract ultrasonic examination aided developer according to claim 1, wherein a gel temperature of the gastrointestinal tract ultrasonic examination aided developer is 20-30° C., a viscosity of the gastrointestinal tract ultrasonic examination aided developer decreases when a temperature is lower than the gel temperature, and the viscosity of the gastrointestinal tract ultrasonic examination aided developer increases when the temperature is higher than the gel temperature; and the viscosity of the gastrointestinal tract ultrasonic examination aided developer at 20±0.2° C. is less than or equal to 100 mPa·s, and the viscosity of the gastrointestinal tract ultrasonic examination aided developer at 37±0.2° C. is more than or equal to 500 mPa·s.

7. A method for preparing the gastrointestinal tract ultrasonic examination aided developer according to claim 1, comprising:

taking pure water, controlling a temperature of the pure water to 2-4° C., adding a thickener, a defoamer, a flavoring agent and a preservative into the pure water at a rotation speed of 800-1200 rpm, then adjusting the rotation speed to 50-100 rpm, adding a solid contrast, then adjusting the rotation speed to 800-1200 rpm, adding an osmotic pressure regulator, stirring for 20-40 min, and finally subpackaging to a 500 ml of brown polyester bottle, so as to obtain the gastrointestinal tract ultrasonic examination aided developer.

* * * * *